(12) United States Patent
Sperl et al.

(10) Patent No.: US 6,300,346 B1
(45) Date of Patent: Oct. 9, 2001

(54) INDENYL HYDROXAMIC ACIDS, (HYDROXY) UREAS AND URETHANES FOR TREATING PATIENTS WITH PRECANCEROUS LESIONS

(75) Inventors: Gerhard Sperl; Paul Gross, both of Stockton, CA (US); Klaus Brendel, Tucson, AZ (US); Rifat Pamukcu, Spring House, PA (US); Gary A. Piazza, Highlands Ranch, CO (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/520,667

(22) Filed: Mar. 7, 2000

Related U.S. Application Data

(62) Division of application No. 08/823,863, filed on Mar. 25, 1997, now Pat. No. 6,071,934.

(51) Int. Cl.$^7$ .......................... A61K 31/44; A61K 31/38; A61K 31/17

(52) U.S. Cl. ................. 514/332; 514/333; 514/336; 514/340; 514/342; 514/348; 514/438; 514/595; 514/343

(58) Field of Search ..................... 514/332, 333, 514/336, 340, 341, 342, 343, 348, 438, 595

(56) References Cited

U.S. PATENT DOCUMENTS

| 4,950,680 |   | 8/1990 | Taylor et al. .................. 514/356 |
| 5,401,774 | * | 3/1995 | Pamukcu et al. .............. 514/569 |
| 6,071,934 | * | 6/2000 | Sperl et al. ................... 514/332 |
| 6,121,321 | * | 9/2000 | Sperl et al. ................... 514/569 |

FOREIGN PATENT DOCUMENTS

WO 95/19978  7/1995  (WO) .

\* cited by examiner

*Primary Examiner*—Jerome D. Goldberg
(74) *Attorney, Agent, or Firm*—Robert W. Stevenson

(57) ABSTRACT

Indenyl hydroxamic acids, (hydroxy) ureas and urethanes are useful in the treatment of precancerous lesions and neoplasms.

16 Claims, No Drawings

INDENYL HYDROXAMIC ACIDS, (HYDROXY) UREAS AND URETHANES FOR TREATING PATIENTS WITH PRECANCEROUS LESIONS

This application is a Divisional of prior U.S. application Ser. No. 08/823,863, filed Mar. 25, 1999 now U.S. Pat. No. 6,071,934 entitled "Indenyl Hydroxamic Acids (Hydroxy) Ureas and Urethanes for Treating Patients With Precancerous Lesions," which is incorporated herein by reference.

TECHNICAL FIELD

This invention relates to compounds and methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either by surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e., the cases of so-called common sporadic polyps), polyp removal will be effective to reduce the risk of cancer. In a small percentage of cases (i.e., the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g., hundreds or more) of polyps— literally covering the colon in some cases—making safe removal of the polyps impossible short of surgical removal of the colon.

Because each polyp carries with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer in intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those with high risk genetic factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Unfortunately, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

Recently, several non-steroidal anti-inflammatory drugs ("NSAIDs"), originally developed to treat arthritis, have shown effectiveness in inhibiting and eliminating the polyps. Polyps virtually disappear when the patient take the drug, particularly when the NSAID sulidac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an anti-arthritic agent. The sulfoxide is reported to be converted by liver enzymes to the corresponding sulfide, which is acknowledged to be the active moiety as a prostaglandin inhibitor. The sulfide, however, is associated with the side effects of conventional NSAIDs. The sulfoxide is also known to be metabolized to sulfone compound, which is regarded to be inactive as an inhibitor of prostaglandin synthesis.

SUMMARY OF THE INVENTION

This invention includes a method of treating patients with precancerous lesions or neoplasms by administering a pharmacologically effective amount of a compound of Formula I below to a patient in need of such treatment. Such compositions are effective in eliminating and inhibiting the growth of precancerous lesions and neoplastic cells.

DETAILED DESCRIPTION OF THE INVENTION

As discussed above, this invention is a method of treating a patient with precancerous lesions or neoplasm by administering a pharmacologically effective amount of a compound of the Formula I below, or the pharmaceutically acceptable salt thereof:

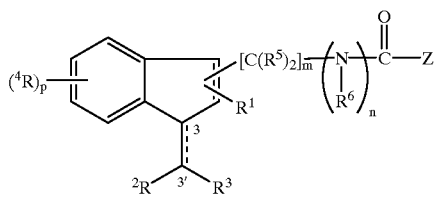

I wherein:

$R^1$ and $R^5$ are independently:
a) hydrogen;
b) lower alkyl;

$R^2$ and $R^3$ are independently:
c) hydrogen;
d) lower alkyl;
e) phenyl substituted with c)-d) hereinabove or $R^7$;
   where $R^7$ is —$OR^8$, —$SR^9$, —$S(O)_nR^9$, —CN, —$CO_2R^8$, or halogen;
   wherein $R^8$ is hydrogen or $R^9$;
   $R^9$ is lower alkyl;
f) heteroaryl substituted with c)-d) hereinabove or $R^7$;
g) lower alkyl monosubstituted with e) to f) hereinabove;

$R^4$ is hydrogen, lower alkyl, lower alkynyl, lower alkenyl, —$OR^8$, —$C(O)R^8$, —$NO_2$, $N(R^8)_2$, —$NR^8C(O)R^8$, —$R^{10}N(R^8)_2$, $SO_2N(R^8)_2$—$SR^9$, —$R^{10}OH$, —$S(O)_nR^9$, —CN, —$CO_2R^8$, —$CON(R^8)_2$, halogen, cycloalkyl, —$R^{10}$, -halogen, or cycloalkoxy; where $R^8$ and $R^9$ are defined hereinabove and $R^{10}$ is lower alkyl;

$R^6$ is hydrogen or OM;

M is hydrogen, a pharmaceutically acceptable cation or —$C(O)R^{11}$; where $R^{11}$ is lower alkyl, or phenyl substituted with hydrogen, lower alkyl or $R^7$;

m is 0 to 4;
n is 1 or 2;
p is 0 to 2;
Z is lower alkyl, $NR^{12}R^{13}$ or —$OR^{13}$;
   where $R^{12}$ is —OM or $R^{13}$; $R^{13}$ is hydrogen, lower alkyl, lower alkynyl, lower alkenyl, lower (substituted) alkyl- (substituted) aryl, cycloalkyl, aryl, heteroaryl, aminoaryl, substituted polyaminalkyl; or where $R^{12}$ and $R^{13}$ are joined to form a heterocyclic ring of 3 to 6 carbon atoms and 1 or 2 heteroatoms selected from N, S or O;

provided that $R^{12}$ is —OM when $R^6$ is hydrogen or n is O; and the dotted line between positions 3 and 3' indicates an optional double bond.

Preferably, and independently, $R^1$ is methyl, $R^2$ is an optionally substituted phenyl, $R^3$ is hydrogen, $R^4$ is a halogen, hydrogen or lower alkyl, $R^5$ is hydrogen, $R^6$ is hydrogen or hydroxide, m is 1, p is 1, and Z is $NR^{12}R^{13}$.

As used herein, alkyl, alkenyl, and alkynyl are intended to include linear and branched structures and combinations thereof.

As used herein, the term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

As used herein, the term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, and the like.

"Lower alkenyl" groups include those alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl and the like.

"Lower alkynyl" groups include those alkynyl groups of 2 to 7 carbon atoms. Examples of lower alkynyl groups include ethynyl, propargyl, 3-methyl-1-pentynyl, 2-heptynyl and the like.

The term "cycloalkyl" refers to a hydrocarbon containing one or more rings having from 3 to 12 carbon atoms, with the hydrocarbon having up to a total of 20 carbon atoms. Examples of cycloalkyl groups are cyclopropyl, cyclopentyl, cycloheptyl, adamantyl, cyclododecylmethyl, 2-ethyl-1-bicyclo[4.4.0]decyl and the like.

The term "cycloalkoxy" refers to an oxygen attached to a hydrocarbon containing one or more rings having from 3 to 12 carbon atoms with the hydrocarbon having up to a total of 20 carbon atoms. Examples of cycloalkoxy groups are cyclopropoxy, cyclopentoxy, cyclododecyloxy, and the like.

The term "heteroaryl" which defines $R^2$, $R^3$ and Z refers to those monocyclic groups of 5 to 7 members containing only one heteroatom selected from N, S, or O in the ring. Examples include furanyl, pyridyl, thienyl and the like.

The term "suitably substituted hydroxylamine hydrochloride" referred to in the Methods section refers to hydroxylamine hydrochloride and lower alkyl hydroxylamine hydrochloride, the latter which includes methylhydroxylamine hydrochloride, ethylhydroxylamine hydrochloride and the like.

The term "halo" or "halogen" includes F, Cl, Br, and I.

It is intended that the definitions of any substituent (e.g., $R^4$, $R^5$, etc.) in a particular molecule be independent of its definitions elsewhere in the molecule. Thus, —$N(R^8)_2$ represents —NHH, —$NHCH_3$, etc.

It is intended that the point of attachment of the $R^1$ substituent may be either at the 1-position or the 2-position of the indene ring and that the $C(R^5)_2$ etc. substituent is attached at the position not occupied by $R^1$. It is intended that the $R^4$ substituent(s) may occupy any of the nonfused positions of the 6-membered ring of the indene.

The heterocycles formed when $R^{12}$ and $R^{13}$ join through N include pyrrolidine, piperidine, morpholine, thiamorpholine, piperazine, and N-methylpiperazine.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of Formula I as an active ingredient or pharmaceutically acceptable salts thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium copper, ferric, ferrous, lithium, magnesium, maganic salts, maganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Thus, M includes the above cations.

When the compound of the present invention is basic, salts may be prepared from pharmaceutically acceptable non-toxic acids, including inorganic and organic acids. Such acids include acetic benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

The present invention includes a method of treating individuals with precancerous lesions by administering pharmaceutically effective amounts of enterically coated compounds of this invention.

As used herein, the term "precancerous lesion" includes syndromes represented by abnormal neoplastic, including dysplastic, changes of tissue. Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, breast and/or skin and related conditions, whether the lesions are clinically identifiable or not.

As used herein, the term "carcinomas" refers to lesions which are cancerous. Examples include malignant melanomas, breast cancer, and colon cancer.

As used herein, the term "neoplasm" refers to both precancerous and cancerous lesions.

Compounds of this invention may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of this invention excipients such as cocoa butter or a suppository wax.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e, oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g., a box or bottle, or both) with suitable printed material (e.g., a package insert) containing indications, directions for use, etc.

In another form, the invention is a method of inhibiting the growth of neoplastic cells by exposing them to a growth-inhibiting effective amount of the compound of Formula [I] above.

In still another form, the invention is a method of regulating apoptosis in human cells by exposing those cells to an effective amount of the compound of Formula [I] above.

The foregoing may be better understood from the following examples, which are presented for purposes of illustration and are not intended to limit the scope of the invention. As used in the following examples, the references to substituents such as R, $R_1$, $R_2$ etc., refer to the corresponding compounds and substituents in the Formula I above.

Representative Compounds

Tables 1 through 5 illustrate compounds representative of the present invention.

TABLE 1

[structure: indene with R4 on benzene ring, R1 at 2-position, =CR2R3 exocyclic, and [CR2^5]m-Y-C(=O)-Z at 3-position]

| EX | [C(R⁵)₂]ₘ | Y | Z | R¹ | R² | R³ | R⁴ |
|---|---|---|---|---|---|---|---|
| 1 | CH₂ | — | N(OH)CH₃ | CH₃ | H | C₆H₄-4-SCH₃ | F |
| 2 | (CH₂)₂ | NOH | CH₃ | CH₃ | H | C₆H₄-4-SCH₃ | F |
| 3 | (CH₂)₂ | NOH | NH₂ | CH₃ | H | C₆H₄-4-SCH₃ | F |
| 4 | (CH₂)₂ | NOH | NHCH₃ | CH₃ | H | C₆H₄-4-SCH₃ | F |
| 5 | (CH₂)₂ | NOH | NHC(CH₃)₃ | CH₃ | H | C₆H₄-4-SCH₃ | F |
| 6 | CH₂ | NH | N(OH)CH₃ | CH₃ | H | C₆H₄-4-SCH₃ | F |
| 7 | (CH₂)₂ | NOH | NH₂ | CH₃ | H | C₆H₄-4-S(O)CH₃ | F |
| 8 | (CH₂)₂ | NOH | NH₂ | CH₃ | H | C₆H₄-4-S(O)₂CH₃ | F |
| 9 | CH₂ | NOH | NH₂ | CH₃ | H | C₆H₄-4-SCH₃ | F |
| 10 | CHCH₃ | NOH | NH₂ | CH₃ | H | C₆H₄-4-SCH₃ | F |
| 11 | (CH₂)₃ | NOH | NH₂ | CH₃ | H | C₆H₄-4-SCH₃ | F |
| 12 | (CH₂)₄ | NOH | NH₂ | CH₃ | H | C₆H₄-4-SCH₃ | F |
| 13 | (CH₂)₂ | NOH | NH₂ | H | C₆H₄-4-SCH₃ | H | H |
| 14 | (CH₂)₂ | NOH | NH₂ | H | C₄H₃O* | H | H |
| 15 | (CH₂)₂ | NOH | NH₂ | H | C₄H₃S** | H | H |

*2-FURYL
**2-THIENYL

TABLE 2

[structure: indene with CH₃ at 3-position, -CH₂CH₂-N(OH)-C(=O)-NH₂ at 2-position, exocyclic =CH-R³]

| EX | R³ |
|---|---|
| 16 | C₆H₄-4-SCH₃ |
| 17 | C₆H₄-4-S(O)CH₃ |
| 18 | C₆H₄-4-S(O)₂CH₃ |

TABLE 3

[structure: indane with -CH₂CH₂-N(OH)-C(=O)-NH₂ at 3-position, R¹ at 2-position, CH₂R³ at 1-position]

| EX | R¹ | —CH₂R³ |
|---|---|---|
| 19 | CH₃ | CH₂C₆H₄-4-SCH₃ |

TABLE 3-continued

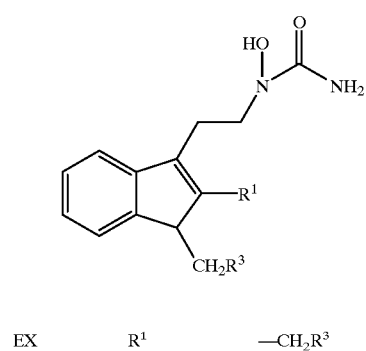

| EX | R¹ | —CH₂R³ |
|---|---|---|
| 20 | H | CH₂CH₃ |

TABLE 4

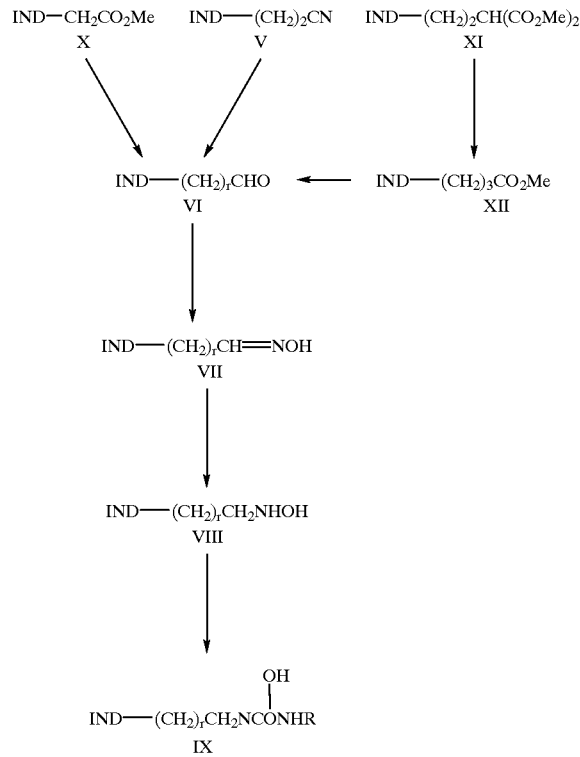

| EX. | Z |
|---|---|
| 21 | NH$^i$Pr |
| 22 | NH(CH$_2$)$_3$NMe$_2$ |
| 23 | NHCH$_2$Ph |
| 24 | NHCH$_2$C(O)NH$_2$ |
| 25 | O$^i$Pr |
| 26 | OCH$_3$ |
| 27 | OCH$_2$CH$_3$ |
| 28 | OCH$_2$CH$_2$OCH$_3$ |

Compounds of the present invention can be prepared according to the following methods. Temperatures are in degree Celsius.

It will be apparent to one skilled in the art that the various functional groups (R$^1$, R$^2$, R$^6$ etc.) must be chosen so as to be compatible with the chemistry being carried out. Such compatibility can often be achieved by protecting groups, or by specific variations in the sequence of the reactions.

When R$^4$ or R$^7$ is S—R$^9$, the corresponding sulfoxides and sulfones can be prepared by oxidation of the sulfides with one or two equivalents of an oxidizing agent such as m-chloroperbenzoic acid or monoperoxyphthalic acid or oxone (Trost, *J. Org. Chem.*, 1988, pg. 532).

Many of the following methods involve a basic hydrolysis of an ester function to obtain the corresponding carboxylic acid. In all cases, the free acid is obtained by acidification of the reaction mixture with a suitable acid such as hydrochloric, sulfuric, acetic, trifluoracetic acid, etc.

METHOD 1

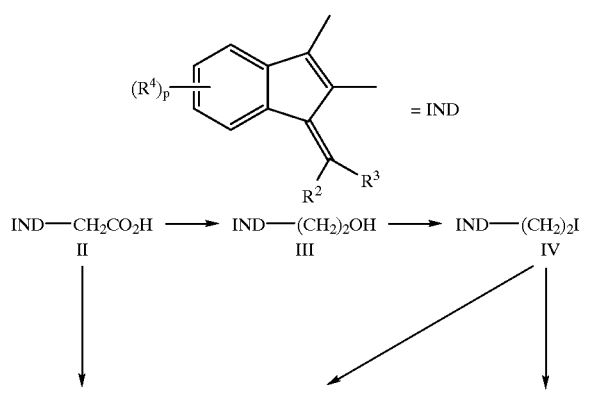

METHOD 1

Intermediate III is prepared by reduction of the indene carboxylic acid II with a reducing agent, such as borane or lithium aluminum hydride, in a suitable organic solvent, such as tetrahydrofuran (THF). The hydroxyethylindene III is converted to the iodoethylindene IV by treatment with an iodine source, such as tetrabutylammonium iodide, in the presence of a hydroxyl-activating agent, such as trifluoromethane sulfonic anhydride, in a suitable organic solvent, such as methylene chloride. The intermediate IV so obtained is converted to the cyanoethylindene V by treatment with a cyanide source, such as potassium cyanide or tetrabutylammonium cyanide, in a suitable organic solvent, such as acetonitrile or dimethylformamide (DMF). The nitrile V is then reduced to the aldehyde VI (r=2) by treatment with a reducing agent, such as diisobutyl aluminum hydride, in a suitable organic solvent such as toluene.

The aldehyde VI so obtained is treated with hydroxylamine hydrochloride in the presence of an organic nitrogen base, such as triethylamine, in a suitable organic solvent, such as ethanol, to provide the oxime VII (r=2). The oxime VII is converted to the hydroxaminoethylindene VIII (r=2) by reducing it with a suitable reducing agent, such as pyridine-borane complex, in the presence of a proton source, such as aqueous hydrochloric acid, in a suitable water-miscible organic solvent, such as ethanol. The hydroxamine VIII so obtained is treated with trimethylsilyl isocyanate in a suitable organic solvent, such as THF, followed by treatment with water to provide a compound IX (r=2, R=H) of the present invention.

Alternatively, the indene carboxylic acid II may be esterified by treating it with thionyl chloride with methanol to provide the ester X. This ester X is converted to the aldehyde VI (r=1) by treatment with a suitable reducing agent, such as diisobutyl aluminum hydride, in a suitable organic solvent, such as toluene. The aldehyde VI so obtained may undergo the sequence of reactions described above to provide a compound IX (r=1, R=H) of the present invention.

Alternatively, the iodoethylindene IV described above is treated with the sodium salt of dimethyl malonate in a suitable organic solvent, such as DMF, to provide the malonate XI. The dimethyl malonate XI is converted to the methyl ester XII by treatment with lithium chloride and water in a suitable water miscible organic solvent, such as dimethyl sulfoxide (DMSO). This ester XII is converted to the aldehyde VI (r=3) as described for ester X. The aldehyde so obtained is converted to a compound IX (r=3, R=H) of the present invention by the sequence of reactions described above.

Reacting compound VIII (r=1) with methyl isocyanate or with t-butyl isocyanate in THF provides compound IX (r=1, R=methyl or t-butyl) of the present invention.

METHOD 3

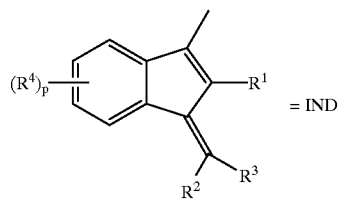

METHOD 2

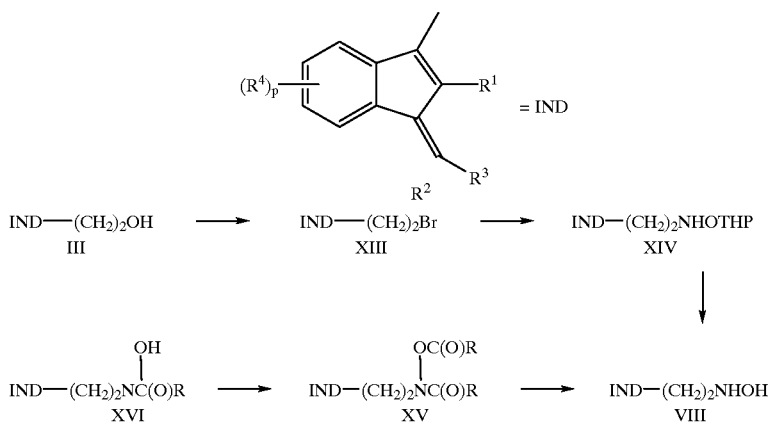

METHOD 2

Intermediate XIII is prepared by treatment of the hydroxyethylindene III with carbon tetrabromide and 1,2-bis(diphenylphosphino)ethane in a suitable organic solvent, such as methylene chloride. The bromoethylindene XIII so obtained is treated with a suitably protected hydroxylamine such as O-(tetrahydropyran-2-yl) hydroxylamine and potassium iodide in a suitable organic solvent, such as DMF or acetone, to provide intermediate XIV. The intermediate XIV is deprotected by treatment with an organic acid such as camphorsulfonic acid in a suitable organic solvent such as methanol to provide the hydroxylaminoethylindene VIII. The intermediate VIII is converted to the acyloxyacylamide XV by treating VIII with a suitable acylating agent, such as an acid chloride (RCOCl) or an acid anhydride ((RCO)$_2$O), and a suitable organic base, such as pyridine, in a suitable organic solvent, such as methylene chloride. The intermediate XV is converted to a compound XVI of the present invention by treatment of XV with a suitable weak base, such as potassium carbonate, in a suitable organic solvent, such as methanol. R is Z in the Formula I compounds.

-continued

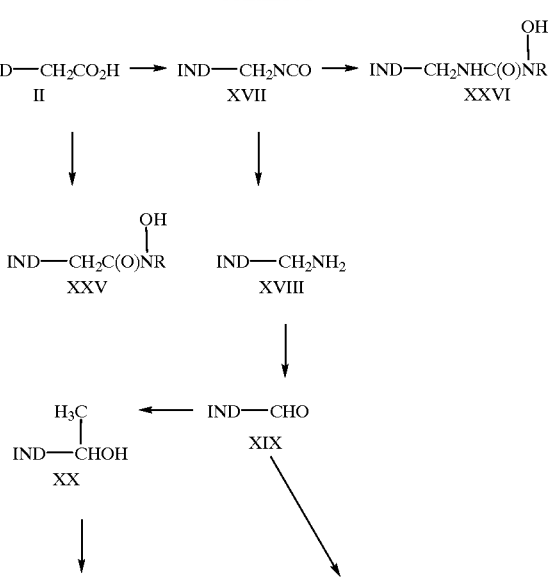

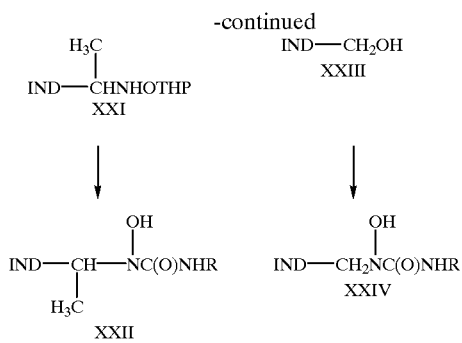

METHOD 3

The indene carboxylic acid II is treated with oxalyl chloride and DMF in a suitable organic solvent such as methylene chloride and the resulting acid chloride is treated with an azide source, such as trimethylsilyl azide or sodium azide, in a suitable organic solvent, such as carbon tetrachloride or acetonitrile, to provide the isocyanate XVII. The isocyanate thus obtained is hydrolyzed to the aminomethylindene XVIII, as the hydrochloride salt, with acetic acid and aqueous hydrochloric acid. The free amine XVIII is obtained by neutralizing the hydrochloride salt with an alkali base, such as sodium hydroxide, in a mixture of water and a suitable organic solvent, such as ethyl acetate (EtOAc). The aminomethylindene XVIII is converted to the aldehyde XIX by first treating the amine with a suitable chlorinating agent, such as t-butyl hypochlorite, in a suitable organic solvent, such as diethyl ether or tetrahydrofuran, followed by a suitable organoalkali base, such as potassium t-butoxide, in a suitable organic solvent, such as ethanol.

The aldehyde XIX thus obtained is reductively alkylated to the hydroxyethylindene XX by treating compound XIX with a suitable methylating agent, such as methyl lithium, in a suitable organic solvent, such as THF and ether, followed by contacting the intermediate with a suitable proton source, such as ammonium chloride in water. The alcohol XX thus obtained is converted to intermediate XXI by treating it with O-(tetrahydropyran-2-yl)-hydroxylamine and a suitable organic acid, such as trifluoroacetic acid, in a suitable organic solvent, such as methylene chloride. The intermediate XXI is deprotected as described in Method 2 for intermediate XIV and is then converted to a compound XXII of the present invention by derivatizing as described in Method 1 for hydroxamine VIII.

Alternately, the aldehyde XIX is reduced by contacting the aldehyde with a suitable reducing agent, such as a combination of cerous chloride and sodium borohydride, in a suitable organic solvent, such as ethanol and THF, to provide the hydroxymethylindene XXIII. The intermediate XXIII is then converted to a compound XXIV of the present invention by the same sequence of reactions as described in Method 2 to provide intermediate VIII followed by the reactions as described in Method 1 to convert intermediate VIII to compound IX.

Alternately, the indene carboxylic acid II is treated with oxalyl chloride and DMF in a suitable organic solvent, such as methylene chloride, and this solution is added to a mixture of a suitable hydroxylamine hydrochloride, such as N-methyl hydroxylamine hydrochloride, and a suitable organic nitrogen base, such as triethylamine, in a suitable organic solvent, such as THF, to provide a compound XXV (R=Me) of the present invention.

Alternately, the indene isocyanate XVII is treated with a suitable hydroxylamine hydrochloride, such as N-methylhydroxylamine hydrochloride, and a suitable organic nitrogen base, such as triethylamine, in a suitable organic solvent, such as THF, to provide XXVI (R=Me) of the present invention.

Method 4

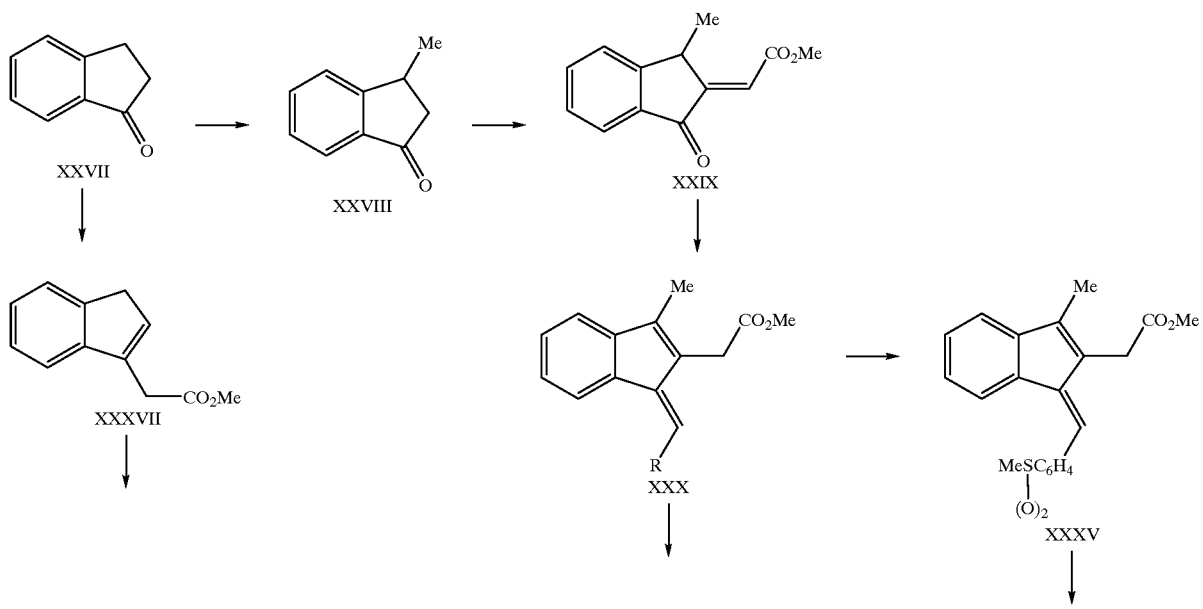

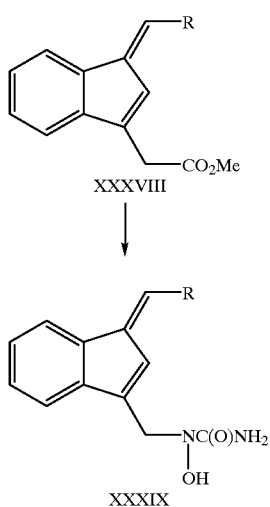

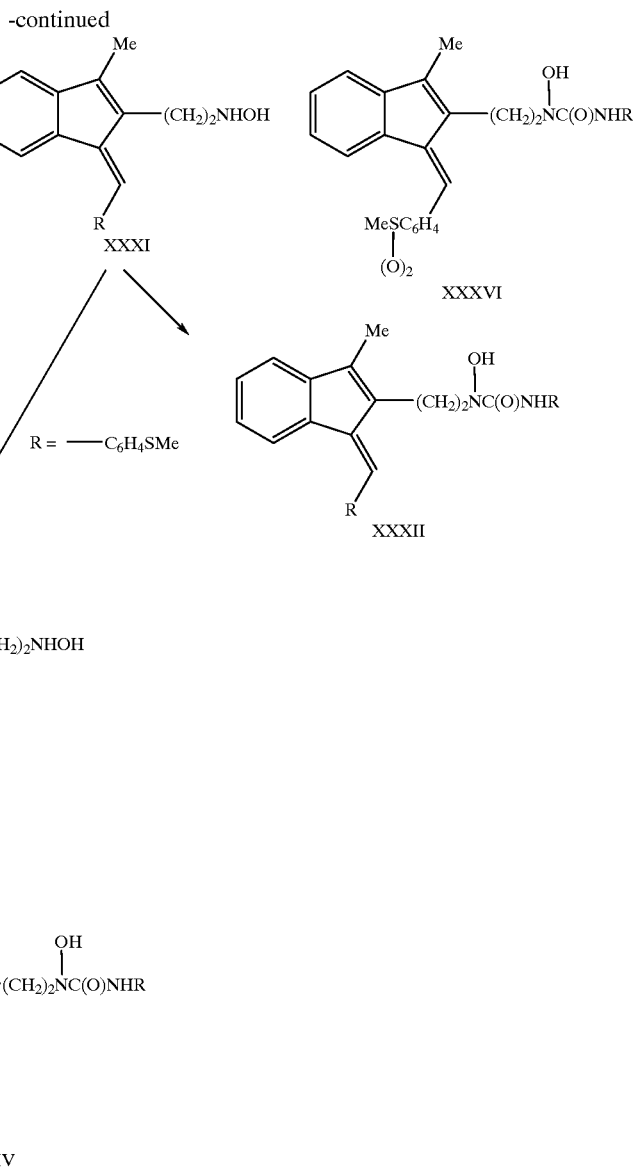

METHOD 4

Intermediate XXVIII is treated with glyoxylic acid hydrate and a suitable strong acid, such as sulfuric acid, in a suitable organic solvent, such as dioxane. The product from this reaction is treated with methanol and thionyl chloride to provide the methyl ester XXIX. The intermediate XXIX is treated with a suitably substituted methylmagnesium halide, such as 4-methylthiobenzylmagnesium bromide, in a suitable organic solvent, such as ether, to provide the intermediate XXX.

Intermediate XXX is reduced by contacting it with a suitable reducing agent, such as diisobutyl aluminum hydride, in a suitable organic solvent, such as THF and toluene. The alcohol obtained this way is oxidized with a suitable oxidizing agent, such as a chromium trioxide/pyridine mixture, in a suitable organic solvent, such as methylene chloride. The aldehyde obtained in this way undergoes the procedure described in Method 1 for aldehyde VI to provide the hydroxamine XXXI. The intermediate XXXI is then treated as described in Method 1 for intermediate VIII to provide a compound XXXII of the present invention.

When the R group in intermediate XXXI is a methylthiophenyl group oxidation of XXXI with approximately one molar equivalent of a suitable oxidizing agent, such as m-chloroperoxy benzoic acid, in a suitable organic solvent, such as methylene chloride provides the sulfoxide XXXIII. The intermediate XXXVIII is then treated as described in Method 1 for intermediate VIII to provide a compound XXXIV of the present invention.

When the R group in intermediate XXX is a methylthiophenyl group oxidation of intermediate XXX with greater than 2 molar equivalents of a suitable oxidizing agent, such as m-chloroperoxy benzoic acid, in a suitable organic solvent, such as methylene chloride, provides the sulfone XXXV. The intermediate XXXV is then treated as described in Method 1 for intermediate X to provide a compound XXXVI of the present invention.

Intermediate XXVII is treated with zinc, methylbromoacetate and iodine in a suitable organic solvent, such as ethyl ether, and after the mixture is refluxed for a sufficient time, such as 3 hours, the mixture is treated with a suitable strong acid, such as aqueous hydrochloric acid, to decompose the zinc complex. The product from this reaction is treated with formic acid which provides the ester intermediate XXXVII. The ester XXXVII is treated with a suitable strong base, such as lithium diisopropyl amide, in a suitable organic solvent, such as THF, then a suitably substituted aldehyde, such as 4-methylthiobenzaldehyde, 2-furaldehyde or 2-thiophene carboxaldehyde, is added. The compound so produced is treated with a suitable strong base, such as Triton B, in a suitable organic solvent, such as methanol, which provides, after acidification with a suitable aqueous acid, such as aqueous hydrochloric acid, and subsequent treatment with diazomethane, provides the intermediate XXXVIII. The intermediate XXXVIII is then treated as described in Method 1 for intermediate X which provides a compound XXXIX of the present invention.

as described in Method 4 for intermediate XXV to provide intermediate XLII which in turn is treated as described in Method 1 for intermediate VIII to provide a compound XLIII of the present invention.

Intermediate XXXVII, described in Method 4, is treated as described above for intermediate XL to provide the ester intermediate XLIV. Intermediate XLIV is treated as described in Method 1 for intermediate VIII to provide a compound XLV of the present invention. R is —CH$_2$-phenyl, as described under definition e) of R$^2$ and R$^3$, or alkyl.

EXAMPLES

The invention is further defined by reference to the following examples, which are intended to be illustrative and not limiting. All temperatures are in degrees Celsius.

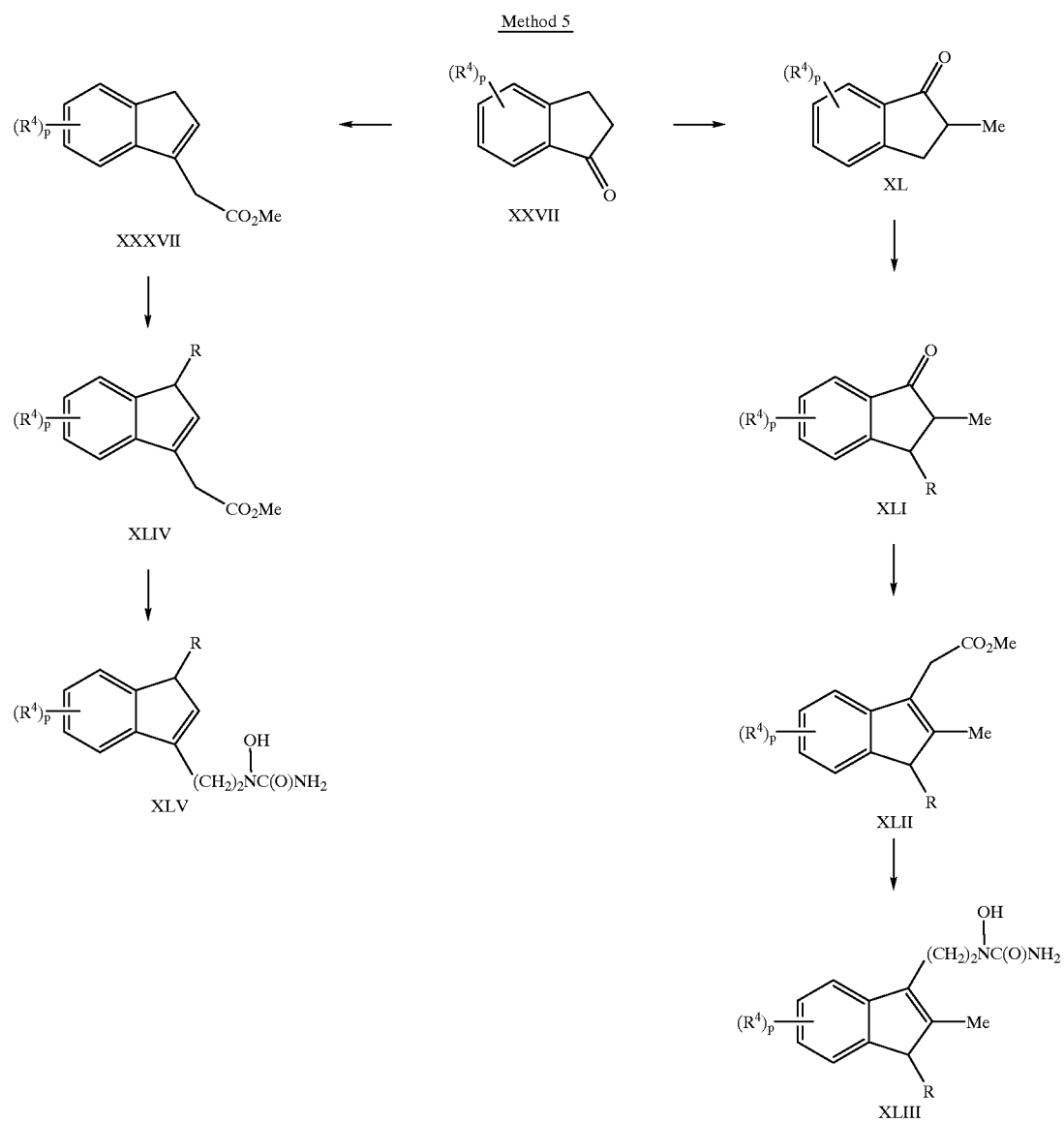

METHOD 5

Intermediate XL is treated with a suitable strong base, such as LDA, in a suitable organic solvent, such as THF and the resulting solution was treated with a suitably substituted alkyl halide (R-hal), such as 4-methylthiobenzyl chloride, providing the intermediate XLI. Intermediate XLI is treated

Example 1

(Z)-N-Hydroxy-N-methyl-5-fluoro-2-methyl-1-(4-methylthiobenzylidene)inden-3-ylacetamide To a suspension of (Z)-5-fluoro-2-methyl-1-(4-methylthiobenzylidene) inden-3-ylacetic acid (U.S. Pat. No.

3,647,858; U.S. Pat. No. 3,654,349; J.O.C. Vol. 42, 1914–1919 (1977) (130 mg, 0.38 mmol) in methylene chloride (3 mL) at room temperature there was added oxalyl chloride (96.5 mg, 0.76 mmol) and one drop of N,N-dimethylformamide (DMF). When gassing had subsided another drop of DMF was added and stirring was continued for 30 minutes. This solution was added, at 0° C., to a mixture of N-methyl hydroxylamine hydrochloride (125 mg, 1.5 mmol) and triethylamine (253 mg, 2.5 mmol) in tetrahydrofuran (THF) (5 mL). After 30 minutes at 0° C., the mixture was diluted with water and ethyl acetate and acidified with iN aqueous HCl. The crude product from the organic extract was crystallized from a mixture of ethyl acetate and hexane to afford the title product as yellow-orange crystals, mp: slow decomp. from 118° C.

Example 2

(Z)-N-{2-[5-Fluoro-2-methyl-1-(4-methylthiobenzylidene)inden-3-yl]ethyl}-N-hydroxyacetamide Step 1

(Z)-N-Acetoxy-{N-2-[5-fluoro-2-methyl-1-(4-methylthiobenzylidene)inden-3-yl]-ethyl}acetamide To a suspension of (Z)-3-(2-hydroxamino-ethyl)-5-fluoro-2-methyl-1-(4-methylthiobenzylidene) indene from Example 3, Method A, Step 4 and Method B, Step 4 (220 mg, 0.645 mmol) in methylene chloride (8 mL) there was added pyridine (253 mg, 3.2 mmol) and acetyl chloride (151 mg, 1.93 mmol). The mixture was stirred at room temperature for 1 hour. Then it was diluted with methylene chloride, washed successively with water, iN aqueous HCl, water, saturated aqueous $NaHCO_3$ and water. After drying over $Na_2SO_4$, the solvent was evaporated and the crude title compound was used as such for the next step.

Step 2

(Z)-N-{2-[5-fluoro-2-methyl-1-(4-methylthiobenzylidene)inden-3-yl]ethyl}-N-hydroxyacetamide The crude diacetylated product from Step 1 was suspended in methanol (10 mL), potassium carbonate (51 mg, 0.368 mmol) was added and the mixture stirred at room temperature for 1 hour. The methanol was evaporated and the residue partitioned between ethyl acetate and water. The residue from evaporation of the organic fraction was triturated with ether and filtered to afford the title product as a yellow solid, mp: 149–151° C., dec.

Example 3

(Z)-N-{2-[5-Fluoro-2-methyl-1-(4-methylthiobenzylidene)inden-3-yl]ethyl}-N-hydroxyurea

METHOD A

Step 1

Methyl (Z)-5-fluoro-2-methyl-1-(4-methylthiobenzylidene)inden-3-ylacetate

To a suspension of (Z)-5-fluoro-2-methyl-1-(4-methylthiobenzylidene)inden-3-ylacetic acid (51 g, 0.15 mol) in methanol (600 mL) at 0° C. there was slowly added thionyl chloride (26.8 g, 0.225 mol). The mixture was then stirred at room temperature for 2 hours and filtered to afford the title compound as a yellow solid, mp 73–75° C.

Step 2

(Z)-5-Fluoro-2-methyl-1-(4-methylthiobenzylidene)inden-3-ylacetaldehyde

To a solution of the ester from Step 1 (3.39 g, 9.57 mmol) in toluene (75 mL) at –70° C., there was slowly added diisobutyl aluminum hydride (1M) in toluene (12 mL, 12 mmol) and the resulting mixture stirred at –70° C. for 45 minutes. Methanol (10 mL) was added slowly at –70° C., then the mixture was warmed to room temperature and water (100 mL) and 1N aqueous HCl (50 mL) were added. The mixture was shaken and the organic layer collected; the aqueous fraction was extracted with ether and the combined organic fractions washed 3 times with water, dried over $MgSO_4$ and evaporated down to a thick oil. The crude title compound was used as such in the next step.

Step 3

(Z)-5-Fluoro-2-methyl-1-(4-methylthiobenzylidene)-3-(2-hydroximinoethyl)indene

A mixture of the acetaldehyde derivative from Step 2 (3.3 g, 10.18 mmol), hydroxylamine hydrochloride (1.42 g, 20.4 mmol), ethanol (25 mL) and triethylamine (2.06 g, 20.4 mmol) was stirred at room temperature for 30 minutes. The solvent was evaporated and the residue was partitioned between ethyl acetate and water. The crude product from the organic phase was purified by column chromatography on silica gel using a 1:2 mixture of ethyl acetate:hexane as eluent. The title compound was obtained as a yellow solid, mp: 146–150° C.

Step 4

(Z)-5-Fluoro-3-(2-hydroxaminoethyl)-2-methyl-1-(4-methylthiobenzylidene)indene

To a suspension of the oxime from Step 3 (2.0 g, 5.9 mmol) in ethanol (35 mL) at 0° C. there was added pyridine-borane (1.1 g, 11.8 mmol) and 12 N aqueous HCl (1.48 mL, 17.75 mmol). The mixture was stirred at 0° C. for 1 hour, then warmed to room temperature. Most of the ethanol was evaporated, the residue was diluted with water and ethyl acetate (the product as hydrochloride salt remains in the organic phase) and was basified with 1N aqueous NaOH. The product obtained from the organic phase was triturated with hexane and was filtered to afford the title compound as a yellow solid, mp: 126° C. dec.

Step 5

(Z)-N-{2-[5-Fluoro-2-methyl-1-(4-methylthiobenzylidene)inden-3-yl]ethyl}-N-hydroxyurea To a solution of the hydroxylamine intermediate from Step 4 (1.62 g, 4.7 mmol) in THF (15 mL) there was added 85% trimethylsilyl isocyanate (954 mg, 7.25 mmol). The mixture was stirred at room temperature for 30 minutes. Water (10 mL) was added and stirring was continued for a further 10 minutes. Ethyl acetate was then added, the organic layer was decanted, washed with brine, dried over $MgSO_4$ and evaporated to dryness. The residue was triturated with ether and filtered to afford the pure title product as a yellow solid, mp: 149° C. dec.

METHOD B

Step 1

(Z)-5-Fluoro-3-(2-hydroxyethyl)-2-methyl-1-(4-methylthiobenzylidene)indene

To a solution of (Z)-5-fluoro-2-methyl-1-(4-methylthiobenzylidene)inden-3-ylacetic acid (1.70 g, 5 mmol) in THF (25 mL) at 0° C. and under nitrogen atmosphere, there was added a solution of borane (1M) in THF (5.5 mL, 5.5 mmol) and the mixture stirred in the cold for 30 minutes, then at room temperature for 2 hours. More borane was added (2.5 mL) and stirring was continued for 1 hour. Water was added slowly (20 mL), the THF was evaporated and the residue partitioned between water and ethyl acetate. The crude product from the organic phase was purified by chromatography on silica gel using a 1:2 mixture of ethyl acetate-hexane as eluent to afford the desired product (1.25 g) as a yellow oil which solidified on standing. This was triturated with hexane and filtered to yield the title compound as a yellow solid, mp 101–103° C.

Step 2

(Z)-3-(2-Bromoethyl)-5-fluoro-2-methyl-1-(4-methylthiobenzylidene)indene

To a solution of the alcohol from Step 1 (4.8 g, 14.7 mmol) and carbon tetrabromide (6.34 g, 19.1 mmol) in methylene chloride (100 mL) at 0° C. there was added, in portions, 1,2-bis(diphenylphosphino)ethane (6.34 g, 17.3 mmol). The mixture was stirred at 0° C. for 1 hour, and the solvent was evaporated. The residue was stirred in a mixture of ethyl acetate and water (150 mL each) for 30 minutes. After filtration, the organic portion of the filtrate was evaporated and the crude product purified by column chromatography on silica gel using 10% ethyl acetate in hexane as eluent to afford pure title compound as a yellow oil which solidified on standing.

Step 3

(Z)-5-Fluoro-2-methyl-1-(4-methylthiobenzylidene)-3-[2-((tetrahydropyran-2-yl)hydroxamino)ethyl] indene A mixture of the bromide derivative from Step 2 (4.86 g, 12.5 mmol), o-(tetrahydropyran-2-yl) hydroxylamine (4.39 g, 37.5 mmol) and potassium iodide (2.08 g, 12.5 mmol) in DMF (50 mL) was heated at 80° C. for 9 hours. After standing at room temperature overnight, the mixture was diluted with ether, washed four times with water, dried over MgSO$_4$ and evaporated to dryness. The crude product was purified by column chromatography on silica gel using a 60:40 mixture of hexane-ethyl acetate as eluent yielding pure title compound as a thick oil which was used in the next step.

Step 4

(Z)-5-Fluoro-3-(2-hydroxaminoethyl)-2-methyl-1-(4-methylthiobenzylidene)indene

A mixture of the indene intermediate from Step 3 (1 g, 2.35 mmol) and (1R)-(–)-l0-camphorsulfonic acid (546 mg, 2.35 mmol) in methanol (30 mL) was refluxed for 3 hours. The methanol was evaporated, the residue dissolved in ethyl acetate and the solution washed successively with water, twice with saturated aqueous sodium bicarbonate, and with water. After drying over Na$_2$SO$_4$, the residue obtained on evaporation of the solvent was triturated with ether and filtered to obtain the title compound as a yellow solid, mp: dec 126° C. which was identical to the product obtained in Method A, Step 4.

Conversion of this intermediate to the title compound was performed following the procedure of Method A, Step 5.

Example 4

(Z)-N-{2-[5-Fluoro-2-methyl-1-(4-methylthiobenzylidene)inden-3-yl]ethyl}-N-hydroxy-N'-methylurea To a solution of (Z)-3-(2-hydroxaminoethyl)-5-fluoro-2-methyl-1-(4-methylthiobenzylidene)-indene from Example 3, Method A, Step 4 (34 mg, 0.1 mmol) in THF (0.5 mL), there was added methyl isocyanate (11.4 mg, 0.2 mmol) and the mixture stirred at room temperature for 1 hour. The solvent was evaporated and the residue triturated with hexane and filtered to afford the title product as a yellow-orange solid, mp: dec 138° C.

Example 5

(Z)-N-{2-[5-Fluoro-2-methyl-1-(4-methylthiobenzylidene)inden-3-yl]ethyl}-N-hydroxy-N'-t-butyl urea Following the procedure of Example 4, but substituting t-butyl isocyanate for methyl isocyanate, the title product was obtained in 75% yield as a yellow solid, mp: dec 134° C.

Example 6

(Z)-N-[5-Fluoro-2-methyl-1-(4-methylthiobenzylidene)-inden-3-ylmethyl]-N'-hydroxy-N'-methyl urea

Step 1

(Z)-5-Fluoro-2-methyl-1-(4-methylthiobenzylidene) inden-3-ylmethyl isocyanate

To a suspension of (Z)-5-fluoro-2-methyl-1-(4-methylthiobenzylidene)inden-3-ylacetic acid (5.0 g, 14.7 mmol) in methylene chloride (50 mL) at room temperature there was added oxalyl chloride (2.8 g, 22 mmol) and DMF (2 drops) and the mixture stirred for 1 hour; the solution was evaporated and the crude acid chloride flushed twice with carbon tetrachloride (20 mL) then suspended in carbon tetrachloride (25 mL) and trimethylsilyl azide (2.53 g, 22 mmol) was added. The mixture was stirred at room temperature for 15 minutes, then gently heated on a steam bath as nitrogen was evolved. The heating was continued until gas evolution ceased, then the mixture was evaporated to afford the crude title compound as an oil which was used as such in the next step.

Step 2

(Z)-N-[5-Fluoro-2-methyl-1-(4-methylthiobenzylidene)inden-3-ylmethyl]-N'-hydroxy-N'-methyl urea To a suspension of N-methyl hydroxylamine hydrochloride (9.82 g, 117.6 mmol) in THF (150 mL) at room temperature there was added triethylamine (16.3 mL, 117.6 mmol) and the mixture stirred for 10 minutes. There was added, over 15 minutes, a solution of the isocyanate from Step 1 in THF (100 mL). After 2 hours of stirring at room temperature, the THF was evaporated and the residue, on trituration with water, afforded a yellow solid which was filtered. This solid was stirred in ether (150 mL) and filtered again. This crude material was chromatographed on silica gel eluting with 5% ethanol in methylene chloride. The more polar component of the mixture was stirred with methylene chloride (50 mL) for 2 hours and filtered and the solid crystallized from ethyl acetate to afford the pure title product as yellow crystals, mp 190–192° C. dec.

Example 7

(Z)-N-{2-[5-Fluoro-2-methyl-1-(4-methylsulfinyl-benzylidene)inden-3-yl]ethyl}-N-hydroxy urea Following the procedure of Example 3, Method A, but substituting (Z)-5-fluoro-2-methyl-1-(4- methylsulfinylbenzylidene)inden-3-ylacetic acid (Sulindac) (U.S. Pat. No. 3,647,858; U.S. Pat. No. 3,654,349; J.O.C. Vol 42, 1914–1919 (1977)) for (Z)-5-fluoro-2-methyl-1-(4-methylthiobenzylidene) inden-3-ylacetic acid as starting material, the title compound was obtained as a yellow solid, mp: 132° C. dec.

Example 8

(Z)-N-{2-[5-Fluoro-2-methyl-1-(4-methylsulfonylbenzylidene)inden-3-yl]ethyl}-N-hydroxy urea cl Step 1

Methyl (Z)-5-fluoro-2-methyl-1-(4-methylsulfonylbenzylidene)inden-3-ylacetate

To a solution of methyl (Z)-5-fluoro-2-methyl-1-(4-methylsulfinyl benzylidene)inden-3-yl acetate from Example 7 (3.7 g, 10 mmol) in methylene chloride (100 mL) there was added 85% m-chloroperoxy benzoic acid (2.54 g, 12.5 mmol) and the mixture was stirred at room temperature for 1 hour. There was added more methylene chloride (100 mL) then calcium hydroxide (5.5 g) and after 10 minutes, the suspension was filtered. The residue obtained by evaporation of the filtrate was stirred with ether (100 mL) at room temperature for 5 hours, then filtered to afford the title compound as a fluffy yellow solid, mp 162–164° C.

Step 2

(Z)-5-Fluoro-3-(2-hydroxyethyl)-2-methyl-1-(4-methylsulfonylbenzylidene)indene

To a solution of the ester from Step 1 (2.7 g, 7 mmol) in THF (20 mL) at 0° C. there was added diisobutyl aluminum hydride (1M) in toluene (17 mL, 17 mmol) and the mixture was stirred at 0° C. for 1 hour, then quenched with methanol (10 mL). Ethyl acetate and 1N aqueous HCl were added and after collection of the organic phase the aqueous phase was extracted once more with ethyl acetate. The combined organic extracts, after washing with water three times and drying over $Na_2SO_4$, afforded on evaporation a yellow residue which was triturated with ether to afford the title compound as a yellow solid, mp: 102–104° C.

Step 3

(Z)-N-{-2-[5-Fluoro-2-methyl-1-(4-methyl-sulfonylbenzylidene)inden-3-yl]ethyl}-N-hydroxy urea Following the procedure of Example 3, Method B, Steps 2–5, but substituting the alcohol intermediate from Step 2 for (Z)-5-fluoro-3-(2-hydroxyethyl)-2-methyl-1-(4-methylthiobenzylidene)indene as starting material, the title compound was obtained as a yellow solid, mp: 187° C.

Example 9

(Z)-N-[5-Fluoro-2-methyl-1-(4-methylthiobenzylidene)inden-3-ylmethyl]-N-hydroxy urea Step 1

(Z)-3-Aminomethyl-5-fluoro-2-methyl-1-(4-methylthiobenzylidene)idene

To a solution of (Z)-5-fluoro-2-methyl-1-(4-methylthiobenzylidene)inden-3-ylmethyl isocyanate from Example 6, Step 1 in acetic acid (80 mL) there was added 12N aqueous HCl (20 mL); the mixture, which became a suspension, was heated on a steam bath for 15 minutes, then diluted with cold water (150 mL) and filtered. The solid was washed with water and ether to afford the amine hydrochloride (5.1 g) as a yellow solid. The free amine, which is unstable on standing, was liberated just prior to use by neutralization with aqueous 2.5N NaOH and extraction with ethyl acetate to afford the title compound as a dark oil.

Step 2

(Z)-5-Fluoro-3-formyl-2-methyl-1-(4-methylthiobenzylidene)indene

To a suspension of freshly liberated amine from Step 1 (11.5 g, 37 mmol) in ether (220 mL) at 0° C. there was added a solution of t-butyl hypochlorite (4.0 g) in ether (10 mL); the mixture was stirred at 0° C. for 5 minutes as a yellow solid formed. The mixture was then allowed to warm up to room temperature and there was slowly added a solution of potassium tert-butoxide (15 g, 133 mmol) in ethanol (200 mL). The mixture was boiled on a steam bath for 10 minutes and then cooled down. There was added 1N aqueous HCl (200 mL) and after stirring for 20 minutes, the mixture was extracted with ether to afford the crude aldehyde which was purified by column chromatography on silica gel, eluting with a 1:5 mixture of ethyl acetate:hexane. The pure title compound was obtained as an oil.

Step 3

(Z)-5-Fluoro-3-hydroxymethyl-2-methyl-1-(4-methylthiobenzylidene)indene

To a solution of the aldehyde from Step 2 (1.0 g, 3.2 mmol) in ethanol (50 mL) and THF (20 mL) there was added cerous chloride (0.79 g, 3.2 mmol) and sodium borohydride (0.13 g, 3.5 mmol). The mixture was stirred at room temperature for 30 minutes, there was added acetone (3 mL) and after 5 minutes the mixture was diluted with brine (100 mL) and extracted with ether (100 mL). The crude material was purified by column chromatography on silica gel, eluting with a 1:5 mixture of ethyl acetate-hexane to afford the title compound as a thick yellow oil.

Step 4

(Z)-N-[5-Fluoro-2-methyl-1-(4-methylthiobenzylidene)inden-3-ylmethyl]-N-hydroxy urea Following the procedure of Example 3, Method B, Steps 2–5, but substituting the alcohol intermediate from Step 3 for (Z)-5-fluoro-3-(2-hydroxyethyl)-2-methyl-1-(4-methylthiobenzylidene)-indene as starting material, the title compound was obtained as yellow needles, mp: 173–176° C. dec. after crystallization from ethyl acetate-hexane.

Example 10

(Z)-N-{1-[5-Fluoro-2-methyl-1-(4-methylthiobenzylidene)inden-3-yl]ethyl}-N-hydroxy urea Step 1

(Z)-5-Fluoro-3-(1-hydroxyethyl)-2-methyl-1-(4-methylthiobenzylidene)indene

To a solution of aldehyde from Example 9, Step 2 (1.5 g, 4.8 mmol) in THF (25 mL) at 0° C. there was added methyl lithium (1.4 M) in ether (3.8 mL, 5.3 mmol) and the mixture stirred at 0° C. for 45 minutes; it was then quenched with saturated aqueous ammonium chloride and extracted with ether to afford crude material which was chromatographed on silica gel to provide the title compound as a reddish syrup.

Step 2

(Z)-5-Fluoro-2-methyl-1-(4-methylthiobenzylidene)-3-[1-((tetrahydropyran-2-yl)-hydroxamino)ethyl]indene To a solution of the alcohol from Step 1 (0.25 g, 0.75 mmol) and 0-(tetrahydropyran-3-yl)-hydroxylamine (0.1 g, 0.85 mmol) in methylene chloride (5 mL) at 0° C. there was slowly added trifluoroacetic acid (0.25 mL, 3.2 mmol) and the mixture was stirred at 0° C. for 2.5 hours. After quenching with brine the mixture was extracted with ether to afford the crude title compound which was used as such in the next step.

Step 3

(Z)-5-Fluoro-3-(1-hydroxaminoethyl)-2-methyl-1-(4-methylthiobenzlidene)indene

The amine intermediate from Step 2 was heated to 50° C. in methanol (20 mL) containing (1R)-(−)-10-camphorsulfonic acid (200 mg) for 18 hours. After quenching with brine the mixture was extracted with ether (100 mL). The crude material was chromatographed on silica gel eluting with a 1:5 mixture of ethyl acetate-hexane to collect the least polar of the two main components of the mixture. This afforded the title compound as a yellow filmy residue which was taken into the next step.

Step 4

(Z)-N-{1-[5-Fluoro-2-methyl-1-(4-methylthiobenzylidene)inden-3-yl]ethyl}-N-hydroxy urea Following the procedure of Example 3, Method A, Step 5, but substituting the indene intermediate from Step 3 for (Z)-5-fluoro-3-(2-hydroxaminoethyl)-2-methyl-1-(4-methylthiobenzylidene)indene as starting material, the title compound was obtained (49 mg) as a yellow solid, mp: 150–152° C.

Example 11

(Z)-N-{3-[5-Fluoro-2-methyl-1-(4-methylthiobenzylidene)inden-3-yl]propyl}-N-hydroxyurea Step 1

(Z)-5-Fluoro-3-(2-iodoethyl)-2-methyl-1-(4-methylthiobenzylidene)indene

To a solution of (Z)-5-fluoro-3-(2-hydroxyethyl)-2-methyl-1-(4-methylthiobenzylidene)indene from Example 3, Method B, Step 1, (9.0 g, 27.6 mmol) and tetrabutylammonium iodide (20.4 g, 55 mmol) in pyridine (4.9 mL, 61 mmol) and methylene chloride (180 mL), cooled to −78° C., there was slowly added trifluoromethane sulfonic anhydride (8 mL, 47.6 mmol). The mixture was stirred at −78° C. for 15 minutes, then at room temperature for one hour. It was then diluted with methylene chloride (200 mL) and washed successively with 10% aqueous sodium thiosulfate, 1N aqueous HCl, saturated sodium bicarbonate, and brine. The crude residue from evaporation of the organic phase was chromatographed on a column of silica gel eluting with a 1:10 mixture of ether-hexane to afford the title compound as a thick yellow oil.

Step 2

(Z)-3-(2-Cyanoethyl)-5-fluoro-2-methyl-1-(4-methylthiobenzylidene)indene

A mixture of the iodide from Step 1 (3.7g, 8.5 mmol) and potassium cyanide (5.5 g, 85 mmol) in DMF (40 mL) was stirred at room temperature for 45 minutes. There was added water (50 mL) and brine (100 mL) and the mixture was extracted with 1:1 ethyl acetate-hexane (4×100 mL); the combined extracts were washed with water (2×50 mL) and brine (1×50 mL), dried and evaporated. The crude residue was chromatographed on silica gel eluting with a 1:2 mixture of ether-ethyl acetate to afford the title compound as a yellow oil.

Step 3

(Z)-5-Fluoro-3-(2-formylethyl)-2-methyl-1-(4-methylthiobenzylidene)indene

To a solution of the nitrile from Step 2 (415 mg, 1.24 mmol) in toluene (4.5 mL) at −78° C. there was added diisobutyl aluminum hydride (1M) in toluene (1.9 mL, 1.9 mmol) and the mixture was stirred at −78° C. for 2 hours; methanol (2 mL) was added and the mixture allowed to warm to room temperature. After partition between ether and water, the residue from evaporation of the organic fraction was chromatographed on silica gel eluting with a 1:2 mixture of ether:hexane to afford the pure title compound as an oil which solidified on standing.

Step 4

(Z)-N-{3-[5-Fluoro-2-methyl-1-(4-methyl-thiobenzylidene)inden-3yl]propyl}-N-hydroxy urea Following the procedure of Example 3, Method A, Steps 3–5, but substituting the aldehyde from Step 3 for (Z)-5-fluoro-2-methyl-1-(4-methylthiobenzylidene)inden-3-ylacetaldehyde as starting material, the pure title compound was obtained after chromatography on silica gel, eluting with a 1:30 mixture of methanol:methylene chloride, as a yellow solid, mp: 145–147° C.

Example 12

(Z)-N-{4-[5-Fluoro-2-methyl-1-(4-methylthiobenzylidene)inden-3-yl]butyl}-N-hydroxy urea Step 1

Dimethyl (Z)-5-fluoro-2-methyl-1-(4-methylthiobenzylidene)inden-3-yl malonate

To a suspension of 60% sodium hydride dispersion in oil (550 mg, 13.8 mmol) in DMF (25 mL) at 0° C. there was added dimethyl malonate (1.6 mL, 13.8 mmol) and the mixture was stirred at 0° C. for 1 hour affording a suspension. To this was added a solution of (Z)-5-fluoro-3-(2-iodoethyl)- 2-methyl-1-(4-methylthiobenzylidene)indene, from Example 11, Step 1, (2.0 g, 4.6 mmol) in DMF (15 mL) and the mixture stirred at 0° C. as gradually a solution resulted; the mixture was then stirred at room temperature for 6 hours. There was added water and brine and the mixture was extracted 3 times with ether. Combined extracts were washed twice with brine, dried and after evaporation the residue was chromatographed on silica gel eluting with a 1:2 mixture of ether-hexane to afford the title compound as an oil.

Step 2

Methyl (Z)-4-[5-fluoro-2-methyl-1-(4-methyl-thiobenzylidene)inden-3-yl]butanoate A mixture of the diester from Step 1 (1.5 g, 3.4 mmol) lithium chloride (0.29 g, 6.8 mmol), water (61 mL, 3.4 mmol)and dimethyl sulfoxide (10 mL) was refluxed for 30 minutes. After having been cooled to room temperature, the mixture was diluted with water (50 mL) and brine (50 mL), then extracted with a 1:1 mixture of ether:ethyl acetate (3×50 mL). The combined extracts were washed twice with water, dried and evaporated to a residue which was purified by chromatography on silica gel eluting with a 1:2 mixture of ether-hexane to afford the title compound as an oil.

Step 3

(Z)-N-{4-[Fluoro-2-methyl-1-(4-methyl-thiobenzylidene)inden-3-yl]butyl}-N-hydroxy urea Following the procedure of Example 3, Method A, Steps 2–5, but substituting the ester of Step 2 for methyl (Z)-5-fluoro-2-methyl-1-(4-methylthiobenzylidene)inden-3-ylacetate as starting material, the N-hydroxy urea derivative was obtained. After chromatography on silica gel, eluting with a 1:20 mixture of methanol:methylene chloride, followed by trituration with ether and filtration, the pure title compound was obtained as a yellow solid; mp: 154–157° C.

Example 13

(E)-N-{2-[1-(4-Methylthiobenzylidene)inden-3-yl]ethyl}-N-hydroxy urea

Step 1

Methyl inden-3-ylacetate

Following the procedure of Example 19, Step 2, but substituting 1-indanone for 2-methyl-3-(4-methylthiobenzyl)-1-indanone, there was obtained the title compound as an oil.

Step 2

Methyl (E)-1-(4-methylthiobenzylidene)inden-3-ylacetate

To a solution of methyl inden-3-ylacetate (2 g, 10.6 mmol) in dry THF (20 mL) at −70° C. was added dropwise a solution of LDA in THF (25.7 mL, 0.87 M, 2.1 eq.). The resulting orange solution was stirred 30 minutes at −70° C. and then 4-methylthiobenzaldehyde (1.6 mL, 11.7 mmol, 1.1 eq.) was added dropwise. The cooling bath was removed and the reaction mixture was left to warm up to room temperature while a precipitate appeared. The reaction mixture was then quenched with a saturated aqueous solution of ammonium chloride and extracted twice with ethyl acetate. The organic phase was washed twice with iN aqueous HCl, then with brine and dried over MgSO$_4$ and evaporated to dryness. The residue was dissolved in methanol (5 mL) and a solution of benzyltrimethylammonium hydroxide in methanol (Triton B, 1.4 M) (6 mL) was added at room temperature. After 10 minutes the reaction mixture was added to 1N aqueous HCl and extracted with ethyl acetate. The organic layer was treated with etheral diazomethane, dried over MgSO$_4$ and evaporated to dryness. The residue was chromatographed on silica gel eluting with a 95:5 mixture of hexane-ethyl acetate to afford the title compound, as an oil.

The E-configuration of the product was established via Nuclear Overhauser effect (NOE) experiments.

Step 3

(E)-N-{2-[1-(4-Methylthiobenzylidene)inden-3-yl]ethyl}-N-hydroxy urea

Following the procedure of Example 3, Method A, Steps 2–5, but substituting the ester of Step 2 for methyl (Z)-5-fluoro-2-methyl-1-(4-methylthiobenzylidene)inden-3-ylacetate as starting material, the title product was obtained in 17% overall yield, mp: 175–176° C.

Example 14

(E)-N-{2- [1-(2-Furylmethine)inden-3-yl]ethyl}-N-hydroxy urea

Following the procedure of Example 13, Steps 2 and 3, but substituting 2-furaldehyde for 4-methylthiobenzaldehyde as starting material, the title product was obtained in 22% overall yield, mp: 140–141° C.

Example 15

(E)-N-(2-[1-(2-Thienylmethine)inden-3-yl]ethyl)-N-hydroxy urea

Following the procedure of Example 13, Steps 2 and 3 but substituting 2-thiophene carboxaldehyde for 4-methylthiobenzaldehyde as starting material, the title product was obtained in 18% overall yield, mp: 145° C.

Example 16

(Z)-N-{2-[3-Methyl-1-(4-methylthiobenzylidene)inden-2-yl]ethyl}-N-hydroxy urea

Step 1

1-Methyl-3-oxo-2-indenylidene acetic acid

A mixture of 3-methylindan-1-one (J.C.S. Chem. Comm. 1973, 636) (2.0 g, 13.7 mmol), glyoxylicacid hydrate (12.6 g, 137 mmol), dioxane (96 mL) and sulfuric acid (8.2 mL) was stirred at 95° C. for 45 minutes. Water (100 mL) was added, and the dioxane evaporated. The residual aqueous suspension was diluted with water and filtered to afford the title compound as a yellow solid.

Step 2

Methyl 1-methyl-3-oxo-2-inden ylidene acetate

To a solution of the acid from Step 1 (1.25 g, 6.2 mmol) in methanol (20 mL) there was slowly added thionyl chloride (1.1 g, 9.3 mmol) and the mixture stirred at room temperature for 22 hours. On concentration to a small volume, a solid crystallized out and was filtered to afford the title ester as light yellow crystals, mp: 96–97° C.

Step 3

Methyl (Z)-3-methyl-1-(4-methylthiobenzylidene)inden-2-ylacetate

To a solution of the ester from Step 2 (560 mg, 2.6 mmol) in ether (5 mL) at 0° C. was added a solution in ether of 4-methylthiobenzylmagnesium chloride (0.21 M, 13.6 mL, 1.1 eq.) . After complete addition, acetic acid (0.2 mL) was added followed by an aqueous solution of ammonium chloride. The reaction mixture was extracted with ethyl acetate and the organic layer was washed with brine, dried over MgSO$_4$ and evaporated to dryness. The crude material was stirred for 2 h at 50–60° C. with a mixture of acetic acid:

water: 12N HCl, 10:1:3 (8 mL). Water was added and the reaction mixture was extracted with ethyl acetate. The organic layer was washed with brine, dried over $MgSO_4$ and evaporated. The crude product was chromatographed on silica gel eluting with a 1:9 mixture of ethyl acetate: hexane to afford the title compound as an oil.

Step 4

(Z)-2-(2-Hydroxyethyl)-3-methyl-1-(4-methylthiobenzylidene)indene

To a solution of the ester from Step 3 (270 mg, 0.83 mmol) in dry THF (5 mL) at 0° C. was added a solution of diisobutyl aluminum hydride (1M) in toluene (2.1 mL, 2.1 mmol, 3.5 eq.). After 1 hour, the reaction mixture was added dropwise to a solution of 1N aqueous HCl and extracted with ethyl acetate. The organic phase was washed with brine, dried over $MgSO_4$ and evaporated to dryness. The crude product was chromatographed on silica gel eluting with a 1:3 mixture of ethyl acetate-hexane to afford pure title compound as a yellow oil.

Step 5

(Z)-3-Methyl-1-(4-methylthiobenzylidene)-inden-2-ylacetaldehyde

A solution of the primary alcohol from Step 4 (1 g, 3.25 mmol) in dichloromethane (10 mL) was added dropwise to a mixture of chromium trioxide (3.3 g, 32 mmol, 10 eq.) in dichloromethane (50 mL) at 0° C. containing pyridine (5.1 mL, 63 mmol, 20 eq.). After 1.5 hour, ether was added to precipitate the chromium salts and the heterogenous mixture was filtered through silica gel and washed with ether. After evaporation to dryness, the residue was purified by chromatography on silica gel eluting with a 15:85 mixture of ethyl acetate-hexane to yield the title compound as a yellow oil.

Step 6

(Z)-N-{2-[3-Methyl-1-(4-methylthiobenzylidene)inden-2-yl]ethyl}-N-hydroxy urea

Following the procedure of Example 3, Method A, Steps 3–5, but substituting the aldehyde of Step 5 for (Z)-5-fluoro-2-methyl-1-(4-methylthiobenzylidene)inden-3-ylacetaldehyde as starting material, the title compound was obtained, mp: 120–122° C.

Example 17

(Z)-N-{2-[3-Methyl-1-(4-methylsulfinylbenzylidene)inden-2-yl]ethyl}-N-hydroxy urea Step 1

(Z)-2-(2-hydroxaminoethyl)-3-methyl-1-(4-methylsulfinylbenzylidene)indene

To a solution of the hydroxylamine from Example 16, Step 6 (130 mg, 0.40 mmol) in dichloromethane (5 mL) at 0° C. was added in one portion 850% m-chloroperoxy benzoic acid (90 mg, 0.44 mmol, 1.1 eq.). After 45 minutes the reaction mixture was diluted with dichloromethane and washed successively with 1N aqueous sodium hydroxide, water, brine, dried over $MgSO_4$ and evaporated to dryness. The residue was chromatographed on silica gel eluting with a 30:1 mixture of dichloromethane:methanol to yield the title compound as yellow oil.

Step 2

(Z)-N-{2-[3-Methyl-1-(4-methylsulfinylbenzylidene)inden-2-yl]ethyl}-N-hydroxy urea Following the procedure of Example 3, Method A, Step 5, but substituting the hydroxylamine of Step 1 for (Z)-5-fluoro-3-(2-hydroxaminoethyl)-2-methyl-1-(4-methylthiobenzylidene)indene as starting material, the N-hydroxy urea derivative was obtained. After chromatography on silica gel eluting with a 5:95 mixture of methanol:methylene chloride, the pure title compound was obtained in 9% yield, mp: 166–169° C.

Example 18

(Z)-N-{2-[3-Methyl-1-(4-methylsulfonylbenzylidene)inden-2-yl]ethyl}-N-hydroxy urea Step 1

Methyl (Z)-3-methyl-1-(4-methylsulfonylbenzylidene)inden-2-ylacetate

To a solution of methyl (Z)-3-methyl-1-(4-methylthiobenzylidene) indene-2-yl acetate from Example 16, Step 3, (1 g, 3.1 mmol) in dichloromethane (30 mL) at 0° C. was added in one portion 85% m-chloroperoxy benzoid acid (1.6 g, 7.7 mmol, 2.5 eq.). The reaction mixture was stirred at 0° C. for 30 minutes, then diluted with dichloromethane and washed successively with an aqueous solution on 1N sodium hydroxide, brine, dried over $MgSO_4$ and evaporated to dryness. The crude product was purified by flash chromatography eluting with a 65:34 mixture of hexane-ethyl acetate to afford the title compound.

Step 2

(Z)-N-{2-[3-Methyl-1-(4-methylsulfonylbenzylidene)inden-2-yl]ethyl}-N-hydroxy urea Following the procedure of Example 3, Method A, Steps 2–5, but substituting the ester from Step 1 for (Z)-5-fluoro-2-methyl-1-(4-methylthiobenzylidene)inden-3-ylacetate as starting material, the title compound was obtained in 27% overall yield, mp: 140–142° C.

Example 19

N-{2-[2-Methyl-1-(4-methylthiobenzyl)inden-3-yl]-ethyl}-N-hydroxy urea

Step 1

2-Methyl-3-(4-methylthiobenzyl)-1-indanone

To a cooled solution (−70° C.) of LDA (1 M) in THF (37 mL) was added dropwise a solution of 2-methyl-1-indanone (J.A.C.S. Vol. 98, 8119–8124 (1976)) (2.5 g, 17 mmol) in THF (20 mL). The resulting dark red solution was stirred at room temperature for 3 hours, then cooled to −20° C. and a solution for 4-methylthiobenzyl chloride (3.1 g, 18 mmol) in THF (15 mL) was added slowly. The addition completed, the reaction mixture was stirred at −20° C. for 30 minutes before being quenched with 3N aqueous HCl (50 mL) and brine (50 mL). The product was extracted with ether, dried over $MgSO_4$ and evaporated to dryness. The oily residue was chromatographed on silica gel eluting with a 1:5 mixture of ethyl acetate-hexane to afford the pure title compound as an oil.

Step 2

Methyl 2-methyl-3-(4-methylthiobenzyl)inden-1-ylacetate

To a solution of the indanone derivative from Step 1 (885 mg, 3.14 mmol) in ether (20 mL) were added successively zinc (840 mg, 12.8 mmol), methyl bromoacetate (0.5 mL, 5 mmol) and iodine (200 mg). The reaction mixture was refluxed for 3 hours, then cooled to 0° C. and 6N aqueous HCl was added dropwise until the zinc complex was completely decomposed. The organic layer was decanted, washed with brine, dried over $Na_2SO_4$ and evaporated to dryness. The oily residue was dissolved in formic acid and evaporated to dryness to complete the dehydration of the intermediate methyl [1-hydroxy-2-methyl-3-(4-methylthiobenzyl)indan-1-yl]acetate. The resulting oily residue was chromatographed on silica gel eluting with a 1:19 mixture of ethyl acetate-hexane to afford pure title compound as an oil.

Step 3

N-{2-[2-Methyl-1-(4-methylthiobenzyl)inden-3-yl]ethyl}-N-hydroxy urea

Following the procedure of Example 3, Method A, Steps 2–5, but substituting the ester from Step 2 for methyl (Z)-5-fluoro-2-methyl-1-(4-methylthiobenzylidene)inden-3-ylacetate as starting material, the title compound was obtained in 44% overall yield, mp: 163–164° C.

Example 20

N-[2-(1-Ethylinden-3-yl)ethyl]-N-hydroxy urea

Step 1

Methyl (1-ethylinden-3-yl)acetate

To a solution of methyl inden-3-ylacetate from Example 13, Step 1 (1 g, 5.32 mmol) in THF (10 mL) at −70° C. was added dropwise a solution of LDA (12.2 mL, 0.87 M, 2 eq.) in THF. The resulting orange solution was stirred for 30 minutes at −70° C. and then ethyl iodide (0.47 mL, 5.85 mmol) was added dropwise. The cooling bath was removed and the reaction mixture was left to warm to room temperature while a precipitate appeared. The reaction mixture was then quenched with a saturated aqueous solution of ammonium chloride and extracted with ethyl acetate. The organic layer was washed with 1N HCl, then with brine, dried over $MgSO_4$ and evaporated to dryness. The oily residue was chromatographed on silica gel, eluting with a 1:19 mixture of ethyl acetate-hexane to afford pure title compound as an oil.

Step 2

N-[2-(1-ethylinden-3-yl)ethyl]-N-hydroxy urea
Following the procedure of Example 3, Method A, Steps 2–5, but substituting the ester of Step 1 for methyl (Z)-5-fluoro-2-methyl-1-(4-methylthiobenzylidene)inden-3-ylacetate as starting material, the title compound was obtained in 66% overall yield, mp: 81–83° C.

Example 21

(Z)-N-{[5-Fluoro-2-methyl-1-(p-methylsulfonylbenzylidene)inden-3-yl]-methyl}-N'-isopropyl urea Step 1

(Z)-5-Fluoro-2-methyl-1-(p-methylsulfonylbenzylidene)inden-3-ylmethyl isocyanate Following the procedure of Example 6, Step 1, but substituting (Z)-5-Fluoro-2-methyl-1-(p-methylsulfonylbenzylidene)-inden-3-ylacetic acid for (Z)-5-Fluoro-2-methyl-1-(p-methylthiobenzylidene)-inden-3-ylacetic acid as starting material, the title compound was obtained which was used as such in the next step.

Step 2

(Z)-N-{[5-Fluoro-2-methyl-1-(p-methylsulfonylbenzylidene)-inden-3-yl]-methyl}-N'-isopropyl urea To a solution of the isocyanate from Step 1 in toluene was added 1.2 equivalent of isopropylamine. The reaction mixture was kept under reflux for 1 h. After having been cooled to room temperature, the mixture was diluted with n-hexane to form a yellow precipitate, which was filtered off, and was recrystallized from $CH_2Cl_2$, to give the title compound as a yellow solid (750%), mp: 217° C.

Example 22

(Z)-N-{[5-Fluoro-2-methyl-1-(p-methylsulfonyl-benzylidene)-inden-3-yl]-methyl}-N'-dimethylaminopropyl urea Following the procedure of Example 21, Step 2, and using 3-dimethylaminopropylamine instead of isopropylamine led to the formation of a yellow solid. Recrystallization from toluene gave the pure title compound (78%), mp: 147° C.

Example 23

(Z)-N-{[5-Fluoro-2-methyl-1-(p-methylsulfonyl-benzylidene)-inden-3-yl]-methyl}-N'-benzyl urea Following the procedure of Example 21, Step 2, and using benzylamine instead of isopropylamine led to the formation of a yellow solid. Recrystallization from toluene gave the pure title compound (62%), mp: 204° C.

Example 24

(Z)-N-{[5-Fluoro-2-methyl-1-(p-methylsulfonyl-benzylidene)-inden-3-yl]-methyl}-N'-glycinamide urea Following the procedure of Example 21, Step 2, and using glycinamide instead of isopropylamine led to the formation of a yellow solid. Recrystallization from methanol gave the pure title compound (69%), mp: 210° C.

Example 25

(Z)-N-{[5-Fluoro-2-methyl-1-(p-methylsulfonyl-benzylidene)-inden-3-yl]-methyl}-O-isopropyl urethane Step 1

(Z)-5-Fluoro-2-methyl-1-(p-methylsulfonylbenzylidene)-3-indenylacetyl chloride (Z)-5-Fluoro-2-methyl-1-(p-methylsulfonylbenzylidene)-3-indenylacetic acid (20 g, 53.70 mmol) was suspended in dichloromethane (400 mL). Oxalylchloride (2M in $CH_2Cl_2$; 35 mL; 70 mmol) was added at room temperature. The reaction mixture was refluxed (24 h), and was evaporated to yield the title compound, which was used as such in the next step.

Step 2

(Z)-5-Fluoro-2-methyl-1-(p-
methylsulfonylbenzylidene)-3-indenylacetyl azide (Z)-5-Fluoro-2-methyl-1-(p-
methylsulfonylbenzylidene)-3-indenylacetylchloride (1 g, 2.69 mmol) in dioxane (20 mL) was added dropwise to a cold (0° C.) solution of sodium azide (0.5 g, 7.69 mmol) in water (1.5 mL) at such a rate that the temperature of the mixture would not exceed 5° C. After being stirred (3 h) the reaction mixture was added dropwise into ice water (100 mL). A yellow solid was filtered off, was washed with water (20 mL), was dried in vacuo, and was used as such in the next step.

Step 3

(Z)-N-{[5-Fluoro-2-methyl-1-(p-
methylsulfonylbenzylidene)-inden-3-yl]-methyl}-O-
isopropyl urethane Dry organic azide from Step 2 was heated at reflux in isopropanol (4 h). The solvent was evaporated. The residue was recrystallized from methanol to yield the title compound as a yellow solid (58%), mp: 185° C.

Example 26

(Z)-N-{[5-Fluoro-2-methyl-1-(p-methylsulfonyl-
benzylidene)-inden-3-yl]-methyl}-O-methyl
urethane Following the procedure of Example 25, Step 3 and using methanol instead of isopropanol led to the formation of the title compound, which was recrystallized from $CH_2Cl_2$ (63%), mp: 171° C.

Example 27

(Z)-N-{[5-Fluoro-2-methyl-1-(p-methylsulfonyl-
benzylidene)-inden-3-yl]-methyl}-O-ethyl urethane Following the procedure of Example 25, Step 3 and using ethanol instead of isopropanol led to the formation of the title compound, which was recrystallized from methanol (63%), mp: 135° C.

Example 28

(Z)-N-{[5-Fluoro-2-methyl-1-(p-methylsulfonyl-
benzylidene)-inden-3-yl]-methyl}-O-methoxyethyl
urethane Following the procedure of Example 25, Step 3 and using methoxyethanol instead of isopropanol led to the formation of the title compound, which was recrystallized from methanol (80%), mp: 162° C.

Biological Effects (A) HT-29

The compounds of this invention were assayed for their effect on the human colon carcinoma cell lines HT-29 and SW-480 obtained from ATCC (Rockville, Md.), representative of precancerous lesions to ascertain the degree of tumor growth inhibition following treatment with compounds of this invention. The cell line employed for these experiments is well characterized, and is used by the United States National Cancer Institute in their screening program for new anticancer drugs. Growth inhibition of this cell line is thought to be indicative of a benefit on precancerous lesions and neoplasms.

Tumor cell cytotoxicity was assessed using the Sulforhodamine B Assay. In this assay, HT-29 tumor cells were plated in 96-well plates and treated with drug-containing media for seven days (continuous exposure). At the end of the exposure period, the cell were fixed and stained with sulforhodamine B (a pink fluorescent dye). The dye was then solubilized, and the optical density of the resulting pink solution determined on a 96-well plate reader. The mean dye intensity of the treated wells was then divided by the mean dye intensity in the control wells (6 wells of each) to determine the effect of the drug on the cells. Dye intensity is proportional to the number of cells or amount of protein per well. The resultant "percent of control" value then represents the degree of growth inhibition caused by the drug.

For each experiment, an $IC_{50}$ value was determined and used for comparative purposes. This value is equivalent to the concentration of drug needed to inhibit tumor cell growth by 50%. $IC_{50}$ values were obtained graphically by connecting the mean values for each drug concentration tested. Each experiment included at least six wells per drug concentration. Concentration was plotted on a log scale on the X-axis. $IC_{50}$ values obtained for the compounds of Examples 21–55 are provided in Table I below.

TABLE I

| EXAMPLE | $IC_{50}$ ($\mu M$) |
| --- | --- |
| 21 | N/A (not very soluble) |
| 22 | 4.4–5.4 |
| 23 | 1.6–3.2 |
| 24 | N/A (not very soluble) |
| 25 | 3.2–4.0 |
| 26 | 4.5–8.0 |
| 27 | 4.1 |
| 28 | 7.1-11.0 |

(B) Apoptosis

Apoptosis was measured based on the amount of fragmented DNA contained in cell lysates. Briefly, SW-480 colon adenocarcinoma cells were plated at a density of 10K cells/well in 180 µl to 96-well microtitre plates ("MTP"), and incubated for 24 hrs. Cells were then treated with 20 µl aliquots appropriately diluted compound, and allowed to incubate for 48 hrs.

After the incubation, samples were prepared according to the following steps. The MTP was centrifuged (15 min., 1000 rpm) and the supernatant was carefully removed by fast inversion of the MTP. The cell pellets in each well were then resuspended in 200 µl lysis buffer and incubated for 45 min. at room temperature to lyse the cells. The lysates were then centrifuged (15 min., 1000 rpm) and 20 µl aliquots of the supernatant (=cytoplasmic fraction) were transferred into the streptavidin coated MTP for analysis. Care was taken not to shake the lysed pellets in the MTP (=cell nucleii containing high molecular weight, unfragmented DNA). Samples were analyzed immediately, because storage at 4 C or −2 C reduces the ELISA-signals.

Samples were then processed according to a DNA fragmentation assay protocol, and dose-response curves were generated based on optical density readings. This assay is the commercially available photometric enzyme-immunoassay sold by Mannheim-Boehringer under the name "Cell Death Detection ELISA$^{plus}$". The assay is based on a quantitative sandwich-enzyme-immunoassay-principle using mouse monoclonal antibodies directed against DNA and histones, respectively. This allows the specific determination of mono and oligonucleosomes in the cytoplasmatic fraction of cell lysates.

According to the vendor, the assay works in the following fashion. The sample (cell-lysate, serum, culture-supernatant etc.) is placed into a streptavidin-coated MTP. Subsequently, a mixture of anti-histone-biotin and anti-DNA-POD are added and incubated for 2 hours. During the incubation period, the anti-histone antibody binds to the histone-component of the nucleosomes and simultaneously fixes the immunocomplex to the streptavidin-coated MTP via its biotinylation. Additionally, the anti-DNA-POD antibody reacts with the DNA component of the nucleosomes. After removal of unbound antibodies by a washing step, the amount of nucleosomes is quantified by the POD retained in the immunocomplex. POD is determined photometrically with ABTS® (2,2'-Azino-di[3-ethylbenzthiazolin-sulfonat])* as substrate.

Fold stimulation (FS=ODmax/ODveh), an indicator of apoptotic response, was determined for each compound data analysis software, or by estimates based on the effective concentration range of each compound (ECR=min. effective dose-min. dose to peak effect). These FS and EC50 values for the tested compounds are listed below in Table II.

TABLE II

| Compound | Fold Stimulation | EC50 ($\mu$M) |
| --- | --- | --- |
| No. 22 | 12.0–4.1 | 75 |
| No. 26 | 5.0–6.8 | 250 |

The compounds of this invention can be formulated with pharmaceutically acceptable carriers into unit dosage forms in a conventional manner so that the patient in need of therapy for precancerous lesions can periodically (e.g., once or more per day) take a compound according to the method of this invention.

The exact initial dose of the compounds of this invention can be determined with reasonable experimentation.

It will be understood that various changes and modifications can be made in the details of procedure, formulation and use without departing from the spirit of the invention, especially as defined in the following claims.

We claim:

1. A method for treating a patient with precancerous lesions sensitive to a compound below, comprising administering to the patient a pharmacologically effective amount of a compound of Formula I:

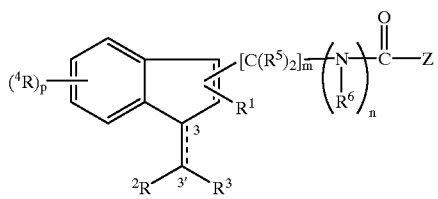

wherein:
$R^1$ and $R^5$ are independently: hydrogen, lower alkyl;
$R^2$ and $R^3$ are independently: hydrogen, lower alkyl, phenyl optionally substituted with lower alkyl or $R^7$; where $R^7$ is —$OR^8$, —$SR^9$, —$S(O)_nR^9$, —CN, —$CO_2R^8$, or halogen; where $R^8$ is hydrogen or $R^9$; and where $R^9$ is lower alkyl. Further, $R^2$ and $R^3$ may be heteroaryl optionally substituted with lower alkyl or $R^7$; or lower alkyl monosubstituted with optionally substituted phenyl or heteroaryl;
$R^4$ is hydrogen, lower alkyl, lower alkynyl, lower alkenyl, —$OR^8$, —$C(O)R^8$, —$NO_2$, $N(R^8)_2$, —$NR^8C(O)R^8$, —$R^{10}N(R^8)_2$, $SO_2N(R^8)_2$—$SR^9$, —$R^{10}OH$, —$S(O)_nR^9$, —CN, —$CO_2R^8$, —CON$(R^8)_2$, halogen, cycloalkyl, —$R^{10}$, halogen, or cycloalkoxy; where $R^8$ and $R^9$ are defined hereinabove and $R^{10}$ is lower alkyl;
$R^6$ is hydrogen or —OM;
M is hydrogen, a pharmaceutically acceptable cation or —$C(O)R^{11}$; where $R^{11}$ is lower alkyl, or phenyl substituted with hydrogen, lower alkyl or $R^7$;
m is 0 to 4;
n is 1 or 2;
p is 0 to 2;
Z is lower alkyl, $NR^{12}R^{13}$ or $OR^{13}$; where $R^{12}$ is —OM or $R^{13}$; $R^{13}$ is hydrogen, lower alkyl, lower alkynyl, lower alkenyl, lower (substituted) alkyl-(substituted) aryl, amino, alkylamino, cycloalkyl, aryl, heteroaryl, adamantyl, substituted polyaminalkyl; or
where $R^{12}$ and $R^{13}$ are joined to form a heterocyclic ring of 3 to 6 carbon atoms and 1 or 2 heteroatoms selected from N, S or O, provided that $R^{12}$ is —OM when $R^1$ is hydrogen or n is 0;
and the dotted line between positions 3 and 3' indicates an optional double bond.

2. The method of claim 1 wherein $R^4$ is a halogen, hydrogen, or lower alkyl.

3. The method of claim 2 wherein $R^4$ is fluoro and p=1.

4. The method of claim 1 wherein the bond between positions 3 and 3' is a double bond.

5. The method of claim 1 wherein $R^3$ is hydrogen.

6. The method of claim 1 wherein $R^2$ is an optionally substituted phenyl.

7. The method of claim 6 wherein $R^2$ is methylsulfonyl phenyl.

8. The method of claim 1 wherein $R^5$ is hydrogen and m=1.

9. A method for inhibiting the growth of neoplastic cells sensitive to a compound below, comprising exposing said cells to an effective amount of a compound of Formula I:

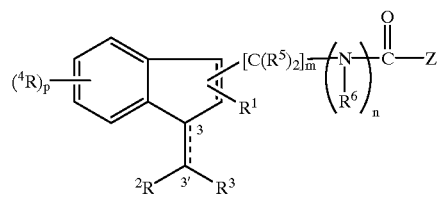

wherein:
$R^1$ and $R^5$ are independently:
hydrogen, lower alkyl;
$R^2$ and $R^3$ are independently: hydrogen, lower alkyl, phenyl optionally substituted with lower alkyl or $R^7$; where $R^7$ is —$OR^8$, —$SR^9$, —$S(O)_nR^9$, —CN, —$CO_2R^7$, or halogen; where $R^8$ is hydrogen or $R^9$; and where $R^9$ is lower alkyl. Further, $R^2$ and $R^3$ may be heteroaryl optionally substituted with lower alkyl or $R^7$; or lower alkyl monosubstituted with optionally substituted phenyl or heteroaryl;
$R^4$ is hydrogen, lower alkyl, lower alkynyl, lower alkenyl, —ORO, —$C(O)R^8$, —$NO_2$, N$(R^8)_2$, —$NR^8C(O)R^8$, —$R^{10}N(R^8_2)$ , $SO_2N(R^8)_2$—$SR^9$, —$R^{10}OH$, —$S(O)_nR^9$, —CN, —$CO_2R^8$, —CON$(R^8)_2$, halogen, cycloalkyl, —$R^{10}$-halogen, or cycloalkoxy;
where $R^8$ and $R^9$ are defined hereinabove and $R^{10}$ is lower alkyl;
$R^6$ is hydrogen or —OM;

M is hydrogen, a pharmaceutically acceptable cation or —C(O)R$^{11}$; where R$^{11}$ is lower alkyl, or phenyl substituted with hydrogen, lower alkyl or R$^7$;

m is 0 to 4;

n is 1 or 2;

p is 0 to 2;

Z is lower alkyl, NR$^{12}$R$^{13}$ or OR$^{13}$; where R$^{12}$ is —OM or R$^{13}$; R$^{13}$ is hydrogen, lower alkyl, lower alkynyl, lower alkenyl, lower (substituted) alkyl-(substituted) aryl, amino, alkylamino, cycloalkyl, aryl, heteroaryl, adamantyl, substituted polyaminalkyl; or where R$^{12}$ and R$^{13}$ are joined to form a heterocyclic ring of 3 to 6 carbon atoms and 1 or 2 heteroatoms selected from N, S or O, provided that R$^{12}$ is —OM when R$^6$ is hydrogen or n is 0;

and the dotted line between positions 3 and 3' indicates an optional double bond.

10. The method of claim 9 wherein R$^4$ is a halogen, hydrogen, or lower alkyl.

11. The method of claim 10 wherein R$^4$ is fluoro and p=1.

12. The method of claim 9 wherein the bond between positions 3 and 3' is a double bond.

13. The method of claim 9 wherein R$^3$ is hydrogen.

14. The method of claim 9 wherein R$^2$ is an optionally substituted phenyl.

15. The method of claim 14 wherein R$^2$ is methylsulfonyl phenyl.

16. The method of claim 9 wherein R$^5$ is hydrogen and m=1.

* * * * *